US009633644B2

(12) United States Patent
Inoue

(10) Patent No.: US 9,633,644 B2
(45) Date of Patent: Apr. 25, 2017

(54) VEHICLE VIBRATION AND NOISE REDUCTION SYSTEM

(71) Applicant: HONDA MOTOR CO., LTD., Minato-ku, Tokyo (JP)

(72) Inventor: Toshio Inoue, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 122 days.

(21) Appl. No.: 14/616,920

(22) Filed: Feb. 9, 2015

(65) Prior Publication Data

US 2015/0228267 A1 Aug. 13, 2015

(30) Foreign Application Priority Data

Feb. 12, 2014 (JP) ................................ 2014-024382
Feb. 5, 2015 (JP) ................................ 2015-020926

(51) Int. Cl.
*G10K 11/16* (2006.01)
*H03B 29/00* (2006.01)
(Continued)

(52) U.S. Cl.
CPC .......... *G10K 11/175* (2013.01); *G10K 11/178* (2013.01); *G10K 2210/129* (2013.01);
(Continued)

(58) Field of Classification Search
CPC ............... G10K 11/175; G10K 11/178; G10K 2210/12821; G10K 2210/3226; G10K 2210/129
See application file for complete search history.

(56) References Cited

U.S. PATENT DOCUMENTS 5,748,748 A 5/1998 Fischer et al.
2005/0056093 A1* 3/2005 Hatano .............. G01P 15/0802 73/488
(Continued)

FOREIGN PATENT DOCUMENTS

DE 19531402 A1 2/1997
EP 0884502 A2 12/1998
(Continued)

OTHER PUBLICATIONS

Office Action dated Aug. 22, 2016 in the corresponding German Application No. 102015202560.8.
(Continued)

*Primary Examiner* — Regina N. Holder
(74) *Attorney, Agent, or Firm* — Carrier Blackman & Associates, P.C.; Joseph P. Carrier; Jeffrey T. Gedeon

(57) ABSTRACT

Provided is a vehicle vibration and noise reduction system that allows the stiffness of the suspension system to be varied while ensuring a favorable noise canceling performance under all conditions. A variable elastic member (4) is incorporated in a vehicle suspension system, and a noise control unit (56) causes a canceling sound to be emitted from a loudspeaker (32) according to a reference signal obtained from a strain sensor (31) provided on the variable elastic member and an error signal obtained from a noise detection unit (33) for detecting noises in the passenger compartment of the vehicle. The noise control unit is configured to change a noise canceling property of the noise control unit depending on the elastic modulus of the variable elastic member.

12 Claims, 5 Drawing Sheets

(51) Int. Cl.
*A61F 11/06* (2006.01)
*G10K 11/175* (2006.01)
*G10K 11/178* (2006.01)

(52) U.S. Cl.
CPC .............. *G10K 2210/12821* (2013.01); *G10K 2210/3226* (2013.01)

(56) References Cited

U.S. PATENT DOCUMENTS

| | | | | |
|---|---|---|---|---|
| 2008/0219465 | A1* | 9/2008 | Miura | G10K 11/16 381/71.4 |
| 2010/0019424 | A1* | 1/2010 | Gagliano | F16F 1/38 267/140.14 |
| 2011/0170701 | A1 | 7/2011 | Sakamoto et al. | |
| 2012/0107556 | A1* | 5/2012 | Zhang | B08B 17/065 428/141 |
| 2013/0136270 | A1 | 5/2013 | Sakamoto et al. | |
| 2013/0158798 | A1* | 6/2013 | Igarashi | B60C 23/20 701/37 |
| 2013/0328254 | A1* | 12/2013 | Kojima | B60K 5/1241 267/140.15 |

FOREIGN PATENT DOCUMENTS

| | | |
|---|---|---|
| JP | 2013-112139 A | 6/2013 |
| JP | 2013-116641 A | 6/2013 |

OTHER PUBLICATIONS

Search Report dated Aug. 22, 2016 in the corresponding German Application No. 102015202560.8.

* cited by examiner

VEHICLE VIBRATION AND NOISE REDUCTION SYSTEM

TECHNICAL FIELD

The present invention relates to a vehicle vibration and noise reduction system, and in particular to a vehicle vibration and noise reduction system that can favorably control the vibration of the vehicle while minimizing noises in the passenger compartment of the vehicle.

BACKGROUND ART

To maximize the comfort of the vehicle occupants, various forms of vehicle noise reduction systems have been proposed. Typically, the noises in the passenger compartment are captured by a microphone, and canceling sound created by inverting the phase of the captured noises is emitted from a loudspeaker to cancel the noises by the canceling sound. See JP2013-112139A, for instance.

In such a vehicle noise reduction system, as the road noise and the engine noise are the primary sources of noises, the signals representing noises from such sources of noises may be used as a reference signal which is to be taken into account by the noise control unit of the vehicle noise reduction system. In particular, the road noise is created by the rolling contact of the tires with the road surface and transmitted to the passenger compartment via the suspension system.

In designing a vehicle noise reduction system, the sound transmission property of the passenger compartment is represented by a transfer function, and the canceling sound is created based on this transfer function. The above mentioned prior art proposes to modify the transfer function depending on the traveling speed of the vehicle.

The suspension system is typically provided with rubber bushes in an effort to improve the ride quality of the vehicle. To improve the ride quality, soft rubber bushes are desirable. However, in order to improve the handling of the vehicle particularly during a cornering, the suspension system is desired to be stiff. Therefore, it has been proposed to use variable elastic bushes that can increase the stiffness of the bushes during cornering or other instances where a stiff suspension is desired, and otherwise decreases the stiffness to ensure a favorable ride quality. See JP2013-116641A, for instance.

Softer bushes are beneficial also in insulating the road noises. When the bushes are stiff, road noises (in particular high frequency components thereof) are transmitted to the passenger compartment with a relatively small attenuation. In conjunction with such a suspension system using variable stiffness bushes, it was discovered that the conventional noise canceling system provides a relatively poor performance in canceling noises when the stiffness of the bushes is increased.

This may be attributed to the fact that the transfer function used by the noise canceling system is unable to represent the actual sound environment under all acoustic conditions, primarily due to the limited positioning and number of the microphones and loudspeakers.

BRIEF SUMMARY OF THE INVENTION

In view of the problems of the prior art, a primary object of the present invention is to provide a vehicle vibration and noise reduction system that allows the stiffness of the elastic bush of the suspension system to be varied while ensuring a favorable noise canceling performance under all conditions.

According to the present invention, such an object can be accomplished by providing a vehicle vibration and noise reducing system, comprising: a noise detection unit for detecting noises in a passenger compartment of a vehicle; a canceling sound emitting unit for emitting canceling sound therefrom; a noise control unit for controlling the canceling sound emitting unit so as to cause the canceling sound to cancel the noises by processing an error signal obtained from the noise detection unit; an elastic member interposed in a transmission path of vibrations from a road surface to the passenger compartment of the vehicle; and a strain sensor for detecting strain in the elastic member; wherein the noise control unit is configured to control the canceling sound emitting unit by taking into account the strain detected by the strain sensor.

Thus, the canceling sound is generated by taking into account the vibration of the elastic member which is a cause of the noises and precedes the emission of noises into the passenger compartment so that the noises in the passenger compartment can be favorably canceled even when the stiffness of the elastic member is high.

According to a preferred embodiment of the present invention, the noise control unit comprises an adaptive filter, and a coefficient of the adaptive filter is updated according to the error signal and the strain of the elastic member. Thereby, an effective noise control can be accomplished.

Preferably, the elastic member comprises a variable elastic member having a variable elastic modulus, and the vehicle vibration and noise reducing system further comprises an elastic member control unit for varying the elastic modulus of the variable elastic member under a prescribed condition.

Thereby, the noises transmitted to the passenger compartment can be reduced while improving the handling and ride quality of the vehicle.

According to a preferred embodiment of the present invention, the noise control unit is configured to change a noise canceling property of the noise control unit depending on the elastic modulus of the variable elastic member.

Thereby, even when the frequency property in the conversion of the vibrations from the road surface to the noises in the passenger compartment via the elastic member has changed owing to a change in the stiffness (elastic modulus) of the elastic member, the control property of the noise control unit can be appropriately adapted so that an effective noise control may be accomplished without regard to the changes in the elastic modulus of the elastic member.

The strain sensor may be used also for detecting the elastic modulus of the variable elastic member.

Thereby, the strain sensor can be used for two purposes at the same time so that the cost of the sensors can be reduced.

Preferably, the noise control unit is configured to increase at least a high frequency component of the canceling sound with an increase in the elastic modulus of the variable elastic member.

Because the high frequency component of the noises increases with an increase in the elastic modulus of the variable elastic member, this allows the noises in the passenger compartment to be controlled in an effective manner.

Preferably, an incremental change in the coefficient of the adaptive filter in each update cycle is temporarily increased when the elastic modulus of the variable elastic member is increased.

When the elastic modulus of the variable elastic member is increased, the deformation of the variable elastic member abruptly decreases so that the canceling sound becomes inadequate temporarily. Therefore, by temporarily increasing the incremental change in the coefficient of the adaptive filter in each update cycle, a drop in the noise canceling performance in such a transient situation can be avoided.

Conversely, when the elastic modulus of the variable elastic member is reduced, the coefficient of the adaptive filter may be immediately updated (or updated upon the softening of the elastic member and in advance of the detection of any error signal) in correspondence to an amount of reduction in the elastic modulus of the variable elastic member so as to prevent the canceling sound from becoming excessive. This may be considered as a feedforward approach as opposed to the normal action which is considered as a feedback approach.

When the elastic modulus (stiffness) of the variable elastic member is reduced, the deformation of the variable elastic member abruptly increases. This in turn causes a sharp increase in the canceling sound so that the canceling sound becomes excessive. By appropriately updating the coefficient of the adaptive filter in advance in such a transient situation, the canceling sound is prevented from becoming excessive.

According to a preferred embodiment of the present invention, the variable elastic member comprises a magneto-viscoelastic elastomer member and an associated variable magnet such as an electromagnet. In particular, the variable magnet may comprise a combination of an electromagnet and a permanent magnet.

Thereby, the elastic modulus of the variable elastic member can be changed easily and with a large dynamic range.

The sensor may comprise a magnetic flux sensor, and the magnetic flux sensor may be encapsulated in the elastic member.

Thereby, the cost of the sensor can be reduced, and the reliability and the durability of the sensor can be improved.

Thus, the present invention can improve the cornering property and the handling of the vehicle while reducing the vibrations and noises that are transmitted to the passenger compartment so that the performance and the market acceptability of the vehicle can be improved.

DETAILED DESCRIPTION OF THE PREFERRED EMBODIMENT(S)

Figure 1:
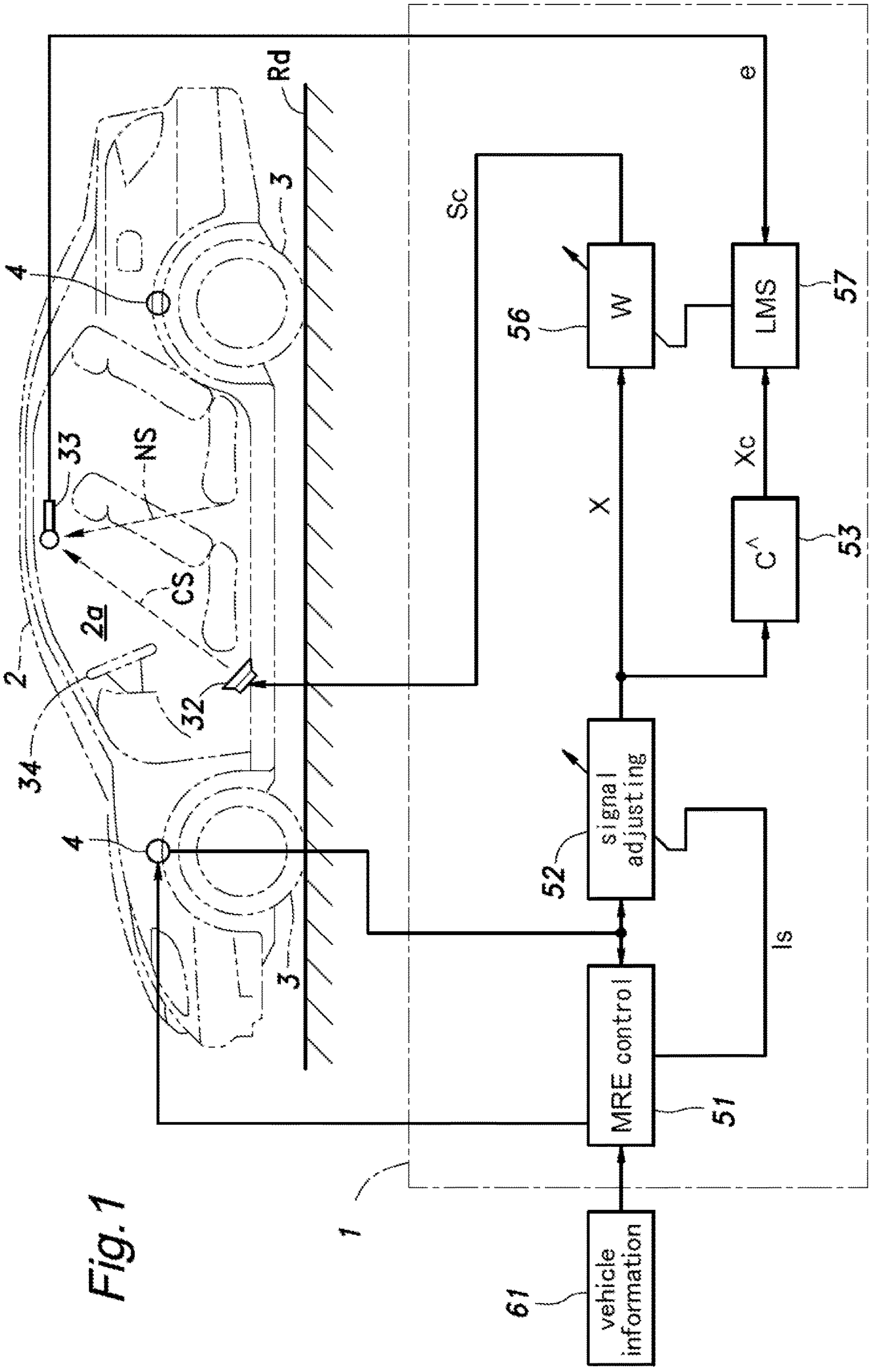
FIG. 1 is a block diagram showing the overall structure of a vehicle vibration and noise reduction system embodying the present invention.

A preferred embodiment of the present invention is described in the following with reference to the appended drawings. FIG. 1 is a block diagram showing the overall structure of a vehicle vibration and noise reduction system embodying the present invention.

An ANC (active noise control) device 1 forming a control unit of the vehicle vibration and noise reduction system shown in FIG. 1 is mounted in a suitable part of a vehicle body 2. An elastic member 4 is interposed between the vehicle body 2 and a suspension system (not shown in the drawings) supporting each wheel 3.

Figure 2:
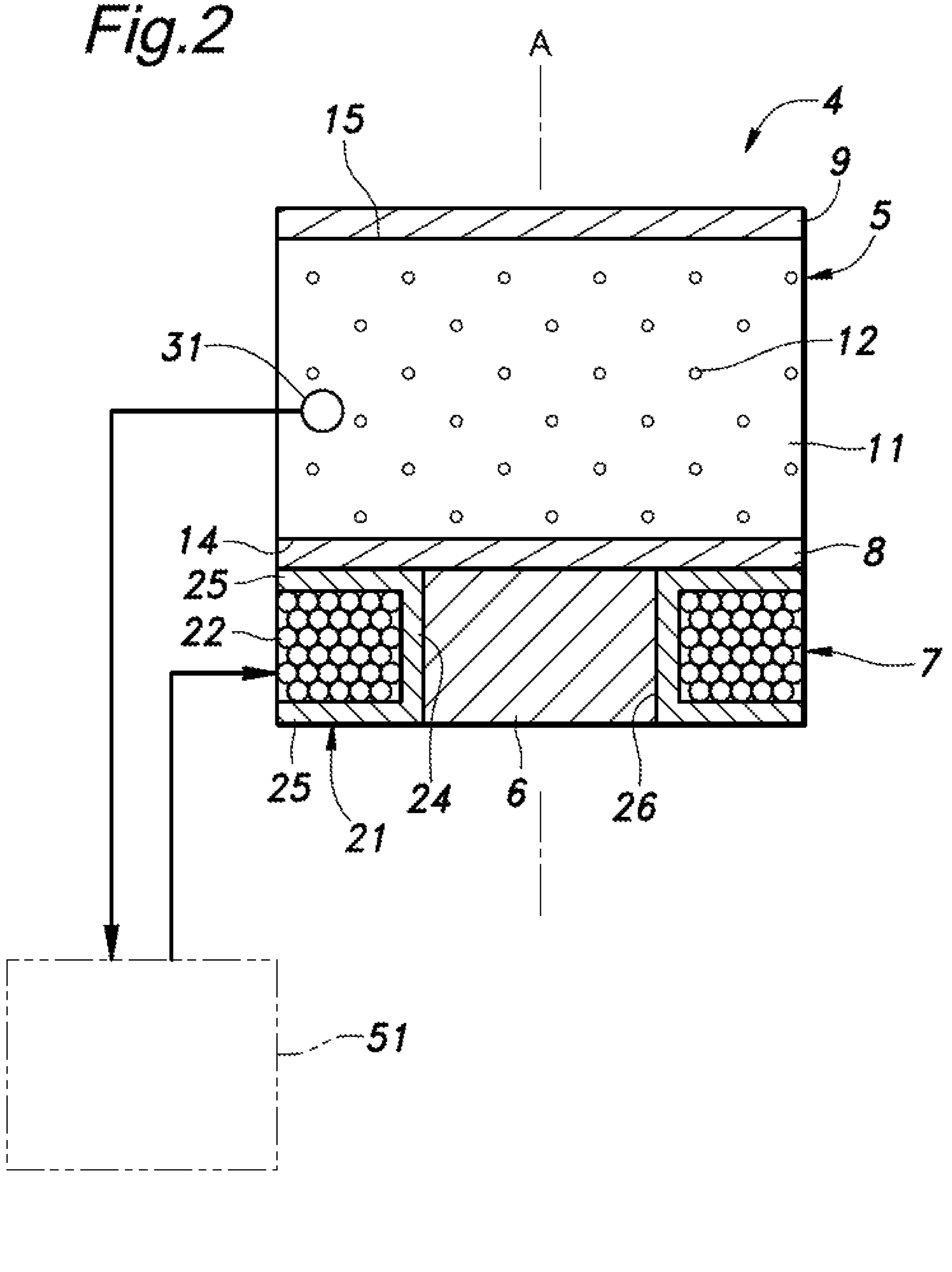
FIG. 2 is a sectional view schematically illustrating an exemplary structure of the elastic member.

FIG. 2 is a sectional view schematically illustrating the elastic member 4. As shown in FIG. 2, the elastic member 4 comprises a magneto-viscoelastic elastomer 5, a permanent magnet 6, an electromagnet 7, a first magnetic member 8 and a second magnetic member 9. In the illustrated embodiment, the magneto-viscoelastic elastomer 5 is provided with a columnar shape with a circular cross section, and the first magnetic member 8 and the second magnetic member 9 are formed as plate members, in particular in the shape of disks. The first magnetic member 8 and the second magnetic member 9 are attached to either end surface of the magneto-viscoelastic elastomer 5. A threaded bolt (not shown in the drawings) may extend from each magnetic member 8, 9 away from the elastic member 4 in a suitable manner so that the suspension system may be supported by the vehicle body 2 via the elastic member 4.

The magneto-viscoelastic elastomer 5 includes a matrix consisting of base elastomer 11 having a suitable viscoelasticity and magnetic particles 12 dispersed in the base elastomer 11. The base elastomer 11 may consist of a per se known high polymer material demonstrating a viscoelastic property at room temperature such as ethylene-propylene rubber, butadiene rubber, isoprene rubber and silicone rubber. The base elastomer 11 has a prescribed central axial line A, and defines a first end surface 14 extending perpendicular to the axial line A at one side thereof and a second end surface 15 extending in parallel with the first end surface 14 on the other side of the first end surface 14. The base elastomer 11 may be given with any shape, such as a rectangular block and a column with a polygonal or circular cross section.

The magnetic particles 12 may consist of any organic or inorganic materials that can magnetically polarize under a magnetic field, and may include pure iron, magnetic pure iron, grain oriented silicon steel, Mn—Zn ferrite, magnetite, metals such as cobalt and nickel, organic materials such as n-(4-methoxybenzylidene)-4-acetoxyaniline and polyaminobenzene polymers, ferrite-dispersed oriented plastic, etc. The magnetic particles may take any shape, such as spherical, needle shaped or planar, and may have any size in a range of, for instance, from 0.01 μm to 500 μm.

The magnetic particles 12 are thus configured to interact weakly to one another when not placed in a magnetic field, and to become strongly attracted to one another under a magnetic action when placed in a magnetic field. During the manufacturing process, the magnetic particles are dispersed in the matrix of uncured elastomer, and the elastomer is cured while the magnetic particles are placed under a magnetic field. Thereby, the magnetic particles are oriented in the direction of the magnetic field, and this increases the dynamic range of the magneto-viscoelastic elastomer. When placed in a magnetic field, the magneto-viscoelastic elastomer increases the stiffness (elastic modulus) thereof, and the increase in the stiffness is substantially proportional to the magnitude of the magnetic field. In the illustrated embodiment, the ratio of the magnetic particles 12 to the base elastomer 11 is in the range of 5% to 60% by volume, and the magnetic particles 12 may be dispersed in the base matrix either uniformly or with a prescribed density gradient.

The first magnetic member 8 and the second magnetic member 9 are made of ferromagnetic or ferrimagnetic material such as ferrite or other iron based material. The first magnetic member 8 and the second magnetic member 9 are thus magnetically polarized when placed in a magnetic field. The first magnetic member 8 is attached to the first end surface 14 of the magneto-viscoelastic elastomer 5 at the major surface thereof, and the second magnetic member 9 is attached to the second end surface 15 of the magneto-viscoelastic elastomer 5 at the major surface thereof. Thus, the magneto-viscoelastic elastomer 5 is interposed between the two magnetic members 8 and 9.

The electromagnet 7 comprises a bobbin 21 and a coil 22 wound around the bobbin 21. The bobbin 21 includes a tubular portion 24 having two open ends and a pair of flanges 25 extending radially outward from either axial end of the tubular portion 24. The coil 22 is wound around the tubular portion 24. One of the flanges 25 is attached to the outer major surface of the first magnetic member 8 at the major surface thereof such that the central axial line of the tubular portion 24 coincides with the axial line A of the magneto-viscoelastic elastomer 5. In other words, the electromagnet 7 is positioned so as to oppose the first magnetic member 8 and the magneto-viscoelastic elastomer 5 in the axial direction. The attachment between the flange 25 and the first magnetic member 8 may be accomplished by using a bonding agent or a mechanical means of attachment.

The permanent magnet 6 may consist of any known permanent magnet such as neodymium magnet, ferrite magnet and alnico magnet, and is positioned in the inner bore 26 of the tubular portion 24 of the electromagnet 7. In this case, the permanent magnet 6 is cylindrical in shape, and has a N pole and a S pole at either axial end thereof. One of the axial ends of the permanent magnet 6 which may be either the N pole or the S pole abuts the first magnetic member 8. The permanent magnet 6 is attached to the tubular portion 24 of the electromagnet 7 and/or the first magnetic member 8. The attachment in this case may also be accomplished by using a bonding agent or a mechanical means of attachment.

The permanent magnet 6 and the electromagnet 7 jointly form a means for applying a magnetic field to the magneto-viscoelastic elastomer 5. The permanent magnet 6 produces a fixed magnetic field, in terms of the magnitude and the direction, while the electromagnet 7 produces a variable magnetic field which can change the magnitude and the direction of the magnetic field by changing the magnitude and the direction of the electric current supplied to the coil 22. When no electric current is supplied to the coil 22, the electromagnet 7 produces no magnetic field. In particular, the magnetic field produced by the electromagnet 7 may be directed either in the same direction or in the opposite direction depending on the direction of the current supplied to the coil 22. It should be noted that the line connecting the N and S poles of the permanent magnet 6, and the line connecting the N and S poles of the electromagnet 7 are in parallel to each other, or more preferably both coaxial to the axial center line A of the magneto-viscoelastic elastomer 5.

The first and second magnetic members 8 and 9 can be magnetized by being polarized in the magnetic fields of the permanent magnet 6 and the electromagnet 7. The first and second magnetic members 8 and 9 extend over the entire surface of the first and second end surfaces 14 and 15 of the magneto-viscoelastic elastomer 5 and/or over the entire end surface of the electromagnet 7. Therefore, the magnetic field produced by the permanent magnet 6 and the electromagnet 7 is evenly applied to the entire volume of the magneto-viscoelastic elastomer 5.

A Hall device 31 is embedded or encapsulated in the base elastomer 11 for detecting the magnetic flux therein, and hence the strain in the base elastomer 11. The detection signal of the Hall device 31 is forwarded to the ANC device 1. The strain in the base elastomer 11 may also be detected by any other strain sensor.

As shown in FIG. 1, a microphone 33 is placed in a suitable part of the passenger compartment 2*a* of the vehicle body 2 as a means for detecting noises, and a loudspeaker 32 is placed near the ears of the vehicle occupant as a means for emitting noise canceling sound. The ANC device 1 controls the noise canceling sound CS that is emitted from the loudspeaker 32 so as to minimize the noises detected by the microphone 33, and performs a feedback control by using the detection signal of the Hall device 31 as will be described hereinafter.

Figure 3:
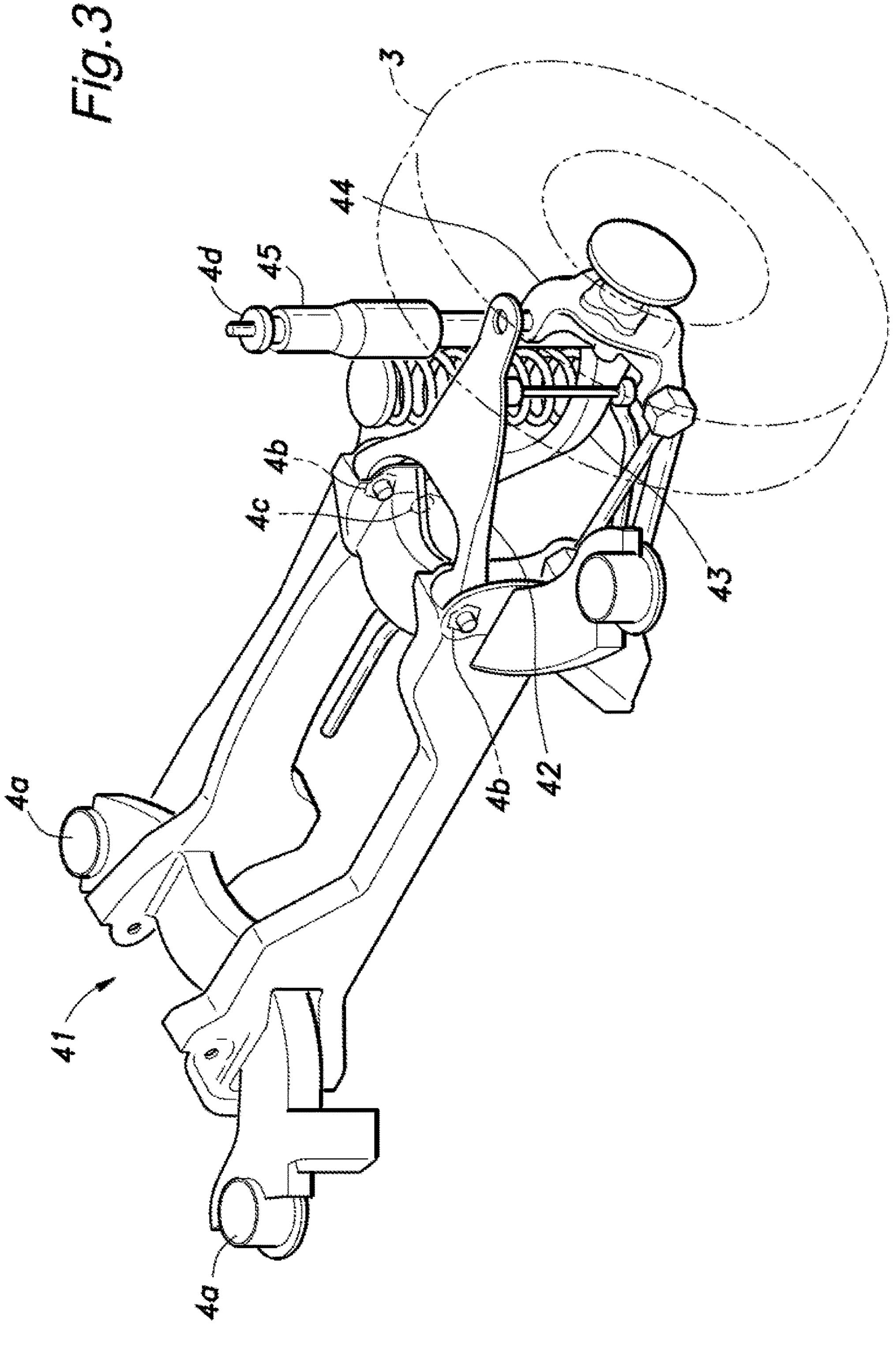
FIG. 3 is a perspective view of an essential part of an exemplary layout of the elastic member.

FIG. 3 is a perspective view of an essential part of an exemplary layout of the elastic members 4, and shows the suspension system supporting the front wheel 3. A rectangular sub frame 41 is attached to the lower surface of the front part of the vehicle body 2. A knuckle 44 is supported on each lateral end of the sub frame 41 via an upper arm 42 and a lower arm 43, and the knuckle 44 rotatably supports the front wheel 3. Because the suspension system is symmetric about the longitudinal center line of the vehicle body, only one of the front wheels 3 is shown in the drawing. A damper device 45 is interposed between the lower arm 43 and the corresponding part of the vehicle body 2.

The sub frame 41 is provided with four sub frame mount bushes 4*a* via which the sub frame 41 is attached to the lower side of the vehicle body 2. The sub frame mount bushes 4*a* are provided on the four corners of the sub frame 41. The base end of the upper arm 42 consisting of an A arm is pivotally connected to the sub frame 41 via a pair of upper arm bushes 4*b*. The base end of the lower arm 43 is pivotally connected to the sub frame 41 via a lower arm bush 4*c*. The upper end of the damper device 45 is connected to the vehicle body 2 via a damper mount rubber 4*d*. These bushes 4*a* to 4*c* and the damper mount rubber 4*d* may each consist of the elastic member 4, and are each placed in a transmission path of vibrations from the road surface Rd to the vehicle body 2 via the wheel 3.

As shown in FIG. 1, the ANC device 1 receives vehicle information (such as vehicle speed, steering angle and steering speed) from a vehicle information detecting unit 61 serving as a means for acquiring vehicle information, and an MRE control unit 51 serving as an elastic modulus changing means for controlling the supply of electric power to the coil 22 of the elastic member 4 of each of the bushes 4*a* to 4*c* and the damper mount rubber 4*d*. The MRE control unit 51 receives the detection signal of the Hall device 31 of each elastic member 4. These detection signals from the Hall devices 31 of the elastic members 4 are also forwarded to a signal adjusting unit 52 also included in the ANC device 1.

The strain signal of each elastic member 4 (MRE bush) detected by the Hall device 31 is converted by the signal adjusting unit 52 into a reference signal (X) to be forwarded to the adaptive filter 56. The signal adjusting unit 52 is provided with a property that can be adjusted by the stiffness control signal Is produced from the MRE control unit 51 under the MRE stiffness control. In other words, the signal adjusting unit 52 is configured to adjust the gain and phase property thereof in processing the strain signal of each elastic member 4 (MRE bush) according to a stiffness control signal Is which corresponds to the electric power supplied from the MRE control unit 51 to the coil 22.

The ANC device 1 further comprises a transfer function setting unit 53 incorporated with a transfer function C^ which models the acoustic system of the passenger compartment for correcting the reference signal X into a corrected reference signal Xc by taking into account the actual acoustic property of the passenger compartment, an adaptive filter 56 for processing the reference signal X into the canceling signal Sc, and a filter coefficient updating unit (LMS) 57 for optimally changing the filter coefficients of the adaptive filter 56 by executing the LMS algorithm by using the error signal e obtained from the microphone 33 and the corrected reference signal Xc as inputs.

The filter coefficient updating unit 57 thus updates the adaptive filter 56 according to the corrected reference signal Xc obtained by processing the reference signal X by using the transfer function C^ between the signal supplied to the loudspeaker 32 and the output signal of the microphone 33, and the error signal e detected by the microphone 33. The adaptive filter 56 produces the canceling signal Sc for reducing the noise in the passenger compartment according to the strain signal from the elastic member 4 (MRE bush) detected by the Hall device 31. The canceling signal Sc is emitted to the passenger compartment via an amplifier (not shown in the drawings) and the loudspeaker 32 that may be those used in the audio system of the vehicle.

FIG. 1 shows an example where the elastic members 4 (RME bushes) are applied to the front suspension system, and the single microphone 33 is placed above the front seat while the single loudspeaker 32 is provided adjacent to the front seat. However, the layout and the numbers of these components are not limited by the illustrated embodiment, but may be freely selected for each particular application. For instance, the elastic member 4 may be provided in association with each of the four wheels. Also, a plurality of elastic members 4 may be used in association with each wheel. For instance, various parts of the suspension system for each wheel such as the upper arm and the lower arm may be individually provided with elastic members. Each of the seats may be provided with a microphone 33, and a plurality of loudspeakers 32 may be arranged in various parts of the passenger compartment, preferably so as to be individually controlled by different control signals.

The ANC device 1 is configured to detect the noises NS (or canceling errors) with the microphone 33, and produce the canceling sound CS from the loudspeaker 32 to cancel the noises under the canceling control process which is discussed in JP2013-112139. Thereby, the noises NS in the passenger compartment can be reduced.

The canceling signal Sc is generated by the adaptive filter 56 according to the reference signal X generated by the signal adjusting unit 52. The filter coefficient updating unit 57 computes the coefficients of the adaptive filter 56 according to an adaptive algorithm (such as a least mean square algorithm) so as to minimize the error signal e at each sampling time. The loudspeaker 32 produces the canceling sound CS according to the canceling signal Sc produced from the adaptive filter 56.

Furthermore, in the illustrated embodiment, the bushes 4*a* to 4*c* and the damper mount rubber 4*d* are arranged in the path of vibration transmission in each of the suspension systems, and the stiffness of each elastic member 4 is increased by receiving electric power from the MRE control unit 51 depending on the vehicle information such that the cornering property and the driving stability may be improved. The vehicle information may include the steering operation of the steering system of the vehicle in the form of such data as the steering angle and the steering speed. The vehicle speed, engine rotational speed of the engine, the gear position and the engine load may also be taken into account among other possible kinds of information.

However, when the stiffness of the elastic member 4 in the path of vibration transmission is increased, the vibration absorbing performance of the elastic member 4 diminishes. As a result, the level of the noises NS in the passenger compartment 2*a* increases, and this is particularly the cases with the high frequency components of the noises NS. The low frequency components of the noises can be effectively canceled by the ANC device 1 without regard to the positioning of the microphone and the loudspeaker and/or the numbers of the microphones and the loudspeakers. However, the high frequency components of the noises NS may not be effectively canceled by the ANC device 1 depending on the positioning of the microphone and the loudspeaker and/or the numbers of the microphones and the loudspeakers owing to the greater directivity and/or the higher attenuation property of the high frequency components of the noises NS.

In the ANC device 1 of the illustrated embodiment, the MRE control unit 51 is configured to control the stiffness of each elastic member 4, and at the same time to cause the signal adjusting unit 52 to change the gain and the phase property thereof, such that the adaptive filter 56 is enabled to cancel the noises NS in a more effective manner based on the adjusted reference signal X. The signal adjusting unit 52 may be incorporated with a map that gives the optimum gain and phase property thereof for each given stiffness of the elastic member 4. For instance, with an increase in the stiffness of the elastic member 4, the high frequency component of the canceling sound may be increased.

Therefore, owing to the ANC device 1 of the illustrated embodiment, the stiffness of the suspension system can be changed so as to optimize the handling of the vehicle without substantially impairing the noise canceling performance. The MRE control unit 51 is configured to control the stiffness of each elastic member 4, and adjust the gain and the phase property of the signal adjusting unit 52.

Figure 4:
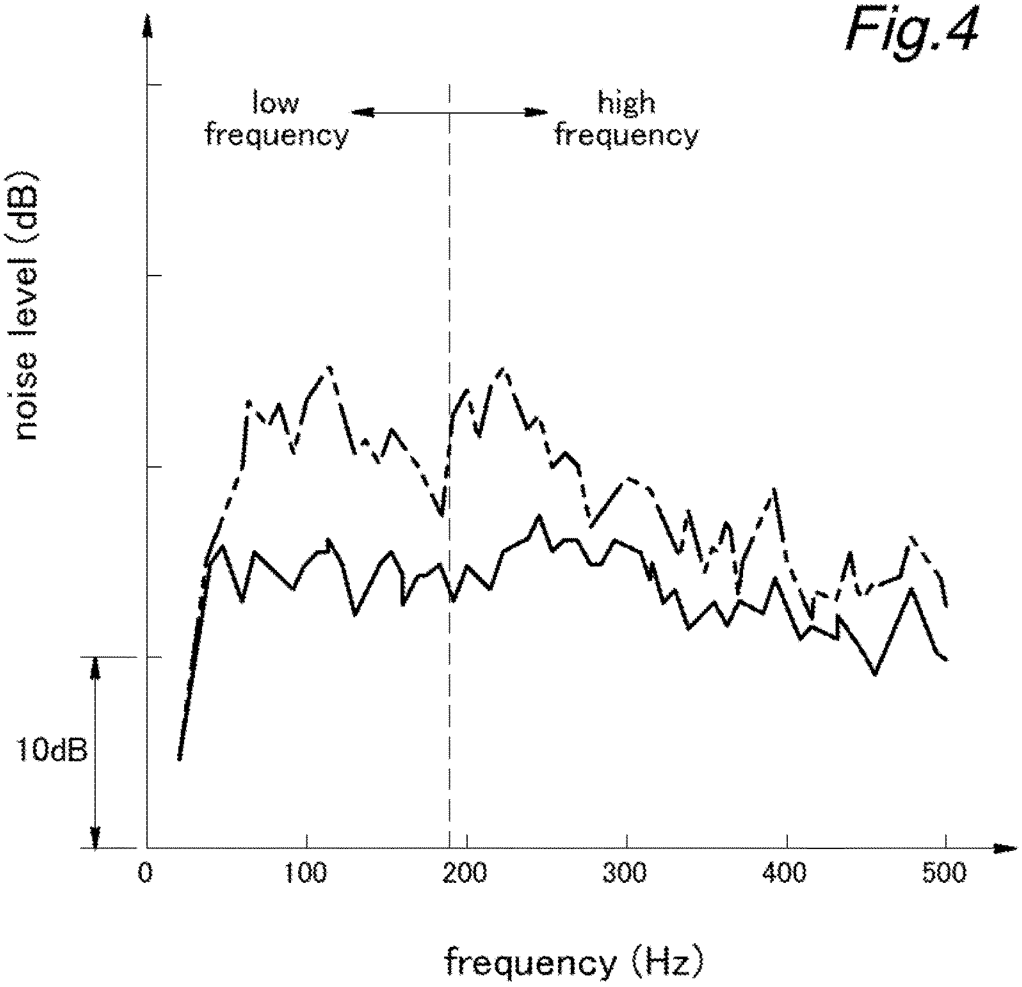
FIG. 4 is graph showing the difference in the noise level made by the control arrangement according to the present invention.

FIG. 4 is a graph showing the difference in the noise level made by the control arrangement according to the present invention. In this graph, the abscissa corresponds to the frequency, and the ordinate corresponds to the noise level. Those frequency components lower than 200 Hz are considered as low frequency components, and those above 200 Hz are considered as high frequency components. The noises are in large part accounted for by the road noises or the vibration of the wheel rolling over the road surface transmitted via the elastic member as the vehicle travels straight on a paved road surface. Normally, the low frequency components are favorably canceled without regard to the stiffness of the elastic member 4. However, when the elastic member 4 is stiffened such as when cornering, the high frequency components are relatively less attenuated by the normal noise canceling action.

However, according to the illustrated embodiment, a favorable noise canceling action can be achieved. In the graph, the double-dot chain dot line indicates the noise level when no noise canceling is being performed. The noise level is high over the entire frequency range. When the noise canceling is being performed, the noise level is favorably reduced over the entire frequency range as indicated by the solid line.

When the stiffness of the elastic member 4 is suddenly increased, because the external force acting on the elastic member 4 normally remains the same, the deformation of the elastic member 4 suddenly decreases. This causes the noise canceling sound to be reduced so that the noise canceling may become inadequate during such a transient condition. Similarly, when the stiffness of the elastic member 4 is suddenly decreased, because the external force acting on the elastic member 4 normally remains the same, the deformation of the elastic member 4 suddenly increases. This causes the noise canceling sound to be increased so that the noise canceling sound may become excessive during such a transient condition. Therefore, certain measures may be taken to eliminate such problems.

FIG. 1 schematically illustrates the principle of the noise canceling action according to the present invention. The error signal e detected by the microphone 33 can be given as the following equation.

$$e=RW^{\hat{}}C^{\hat{}}+d \tag{1}$$

Here, R is the noise source causing the road noise to be transmitted to the passenger compartment, W^ is the transfer function of the adaptive filter 56, and C^ is the transfer function of the acoustic transmission property of the passenger compartment. The noises including the road noise is given by d. By making e=0, the noises in the passenger compartment can be eliminated. As only W^ is variable in this case, the coefficients of the adaptive filter 56 are updated so as to minimize the square of the error signal e. This updating process is performed in each incremental control cycle as given in the following.

$$W_{n+1}=W_n-MeRC^{\hat{}} \tag{2}$$

The maximum incremental change in the coefficients of the adaptive filter 56 for each updating cycle is determined by a step size parameter M. The step size parameter M for the normal condition is determined such that the noise canceling signal is allowed to follow the changes in the noise level without causing any excessive overshoot.

Figure 5A:
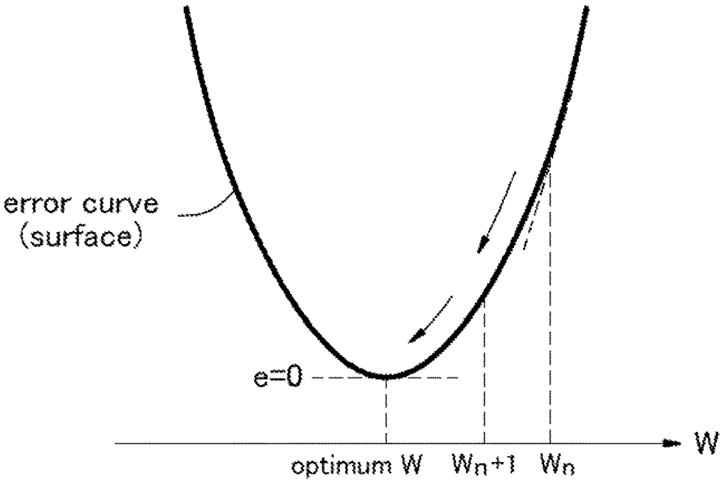
FIG. 5*a* is a diagram illustrating the principle of minimizing the error signal by updating a coefficient of an adaptive filter used in the vehicle vibration and noise reduction system of the present invention.

The coefficients of the adaptive filter 56 are updated so that the error signal e is reduced to zero, and this process may be illustrated as a movement of an operating point on an error curve (or surface) as shown in FIG. 5*a*. MeRC^ corresponds to the slope of this curve (or surface) because a partial derivative of $e^2$ with respect to W yields 2eRC^. The adaptive filter 56 is updated such that the operating point moves in search of a smaller inclination toward the bottom of the error curve (surface).

Figure 5B:
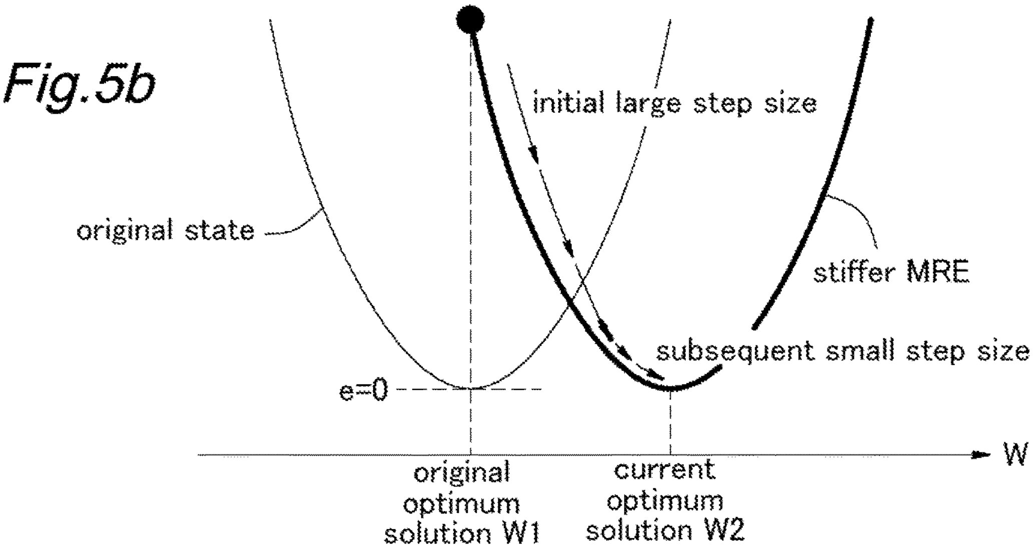
FIG. 5*b* is a diagram similar to FIG. 5*a* showing the process of accelerating the updating of the coefficient when the variable elastic member is stiffened.

Suppose that the stiffness of the elastic member 4 is suddenly increased, and the deformation of the elastic member has thereby suddenly decreased. As a result, the noise canceling signal diminishes, and the resulting shortage of the noise canceling signal causes the noise level to increase. According to the present invention, to minimize the shortage of the noise canceling signal in such a case, the step size parameter M is increased as shown in FIG. 5*b*. Optionally, to minimize the risk of overshooting, the step size parameter M may be varied such that a relatively large step size parameter M is selected when the error signal is large, and the step size parameter is reduced as the error signal diminishes (this may be performed either in a continuous manner or in a stepwise manner).

Figure 5C:
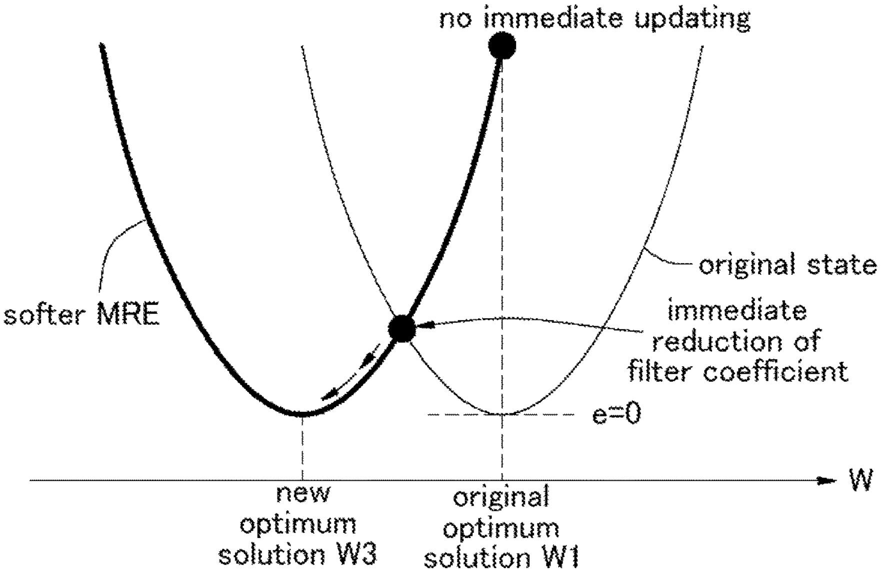
FIG. 5*c* is a diagram similar to FIG. 5*a* showing the process of optimizing the coefficient promptly when the variable elastic member is softened.

Conversely, suppose that the stiffness of the elastic member 4 is suddenly decreased, and the deformation of the elastic member has thereby suddenly increased. As a result, an excessive noise canceling signal is produced, and this excessive noise canceling signal is perceived by human ears as an annoying noise. According to the present invention, to prevent the noise canceling signal to be excessive in such a case, the coefficients of the adaptive filter 56 are appropriately reduced substantially simultaneously as the stiffness of the elastic member 4 is decreased as shown in FIG. 5*c* (this can be achieved by referring to the stiffness control signal Is, for example). Thereby, the noise canceling signal is sharply reduced in synchronism with the decrease in the stiffness of the elastic member 4 so that the annoying noise which may be otherwise produced by the excessive noise canceling signal can be avoided. Thereafter, the coefficients of the adaptive filter 56 are adjusted as appropriate. In this way, it is possible to prevent an annoying sound from being generated due to the noise canceling signal becoming temporarily excessive when the stiffness of the elastic member 4 abruptly decreases. This may be considered as a feedforward approach based on the detected change in the elastic modulus or the command to change the elastic modulus as opposed to the normal action which is considered as a feedback approach based on the detection of the error signal. Therefore, the updating of the coefficients occurs immediately upon the softening of the elastic member 4 and in advance of the detection of any error signal.

As discussed above, the increase in the stiffness of the elastic member diminishes the attenuation of the road noises by the elastic member, particularly in high frequency components thereof. The increase in the high frequency components in the noises causes an inadequate noise canceling action by the ANC device 1 owing to the limitations in the positioning and the number of the loudspeakers and the microphones. Therefore, it is advantageous to increase the amplitude of the canceling signal in a high frequency range when the stiffness of the elastic member is increased. In vehicle applications, there is a severe restriction on the positioning and the number of the loudspeakers and the microphones.

However, according to the present invention, a favorable sound canceling action can be ensured over the entire frequency range in spite of the restriction on the positioning and the number of the loudspeakers and the microphones, only with a slight modification in the noise canceling algorithm. Therefore, a significant cost saving can be achieved.

In the foregoing embodiment, for producing the magnetic field for magnetizing the magneto-viscoelastic elastomer 5, the combination of a permanent magnet and an electromagnet was used, but it is also possible to use only the electromagnet. When a mechanism for moving the permanent magnet toward and away from the magneto-viscoelastic elastomer 5 is provided, it is possible to use only the permanent magnet.

Although the present invention has been described in terms of a referred embodiment thereof, it is obvious to a person skilled in the art that various alterations and modifications are possible without departing from the scope of the present invention which is set forth in the appended claims. The contents of the original Japanese patent applications on which the Paris Convention priority claim is made for the present application as well as the contents of the prior art references mentioned in this application are incorporated in this application by reference.

The invention claimed is:

1. A vehicle vibration and noise reducing system, comprising:

a microphone for detecting noises in a passenger compartment of a vehicle;

a speaker for emitting canceling sound therefrom;

an active noise control device for controlling the canceling sound emitted from the speaker so as to cause the canceling sound to cancel the noises by processing an error signal obtained from the microphone;

an elastic member interposed in a transmission path of vibrations from a road surface to the passenger compartment of the vehicle, wherein the elastic member is incorporated in an elastic bush of a wheel suspension system of the vehicle and is a variable elastic member having a variable elastic modulus which allows a stiffness of the elastic bush of the wheel suspension system to be varied;

a strain sensor for detecting strain in the elastic member; and an elastic member control unit for varying the elastic modulus of the variable elastic member under a prescribed condition, wherein the active noise control device is configured to control the canceling sound emitted from the speaker by taking into account the strain detected by the strain sensor and further by changing a noise canceling property of the active noise control device depending on the elastic modulus of the variable elastic member such that the stiffness of the elastic bush of the suspension system is allowed to be varied while ensuring a noise canceling performance under the prescribed condition.

2. The vehicle vibration and noise reducing system according to claim 1, wherein the active noise control device comprises an adaptive filter, and a coefficient of the adaptive filter is updated according to the error signal and the strain of the elastic member.

3. The vehicle vibration and noise reducing system according to claim 1, wherein the strain sensor is used also for detecting the elastic modulus of the variable elastic member.

4. The vehicle vibration and noise reducing system according to claim 1, wherein the active noise control device is configured to increase at least a high frequency component of the canceling sound with an increase in the elastic modulus of the variable elastic member.

5. The vehicle vibration and noise reducing system according to claim 1, wherein an incremental change in the coefficient of the adaptive filter in each update cycle is temporarily increased when the elastic modulus of the variable elastic member is increased.

6. The vehicle vibration and noise reducing system according to claim 1, wherein the coefficient of the adaptive filter is immediately updated when the elastic modulus of the elastic member is reduced in correspondence to an amount of reduction in the elastic modulus of the variable elastic member so as to prevent the canceling sound from becoming excessive.

7. The vehicle vibration and noise reducing system according to claim 1, wherein the variable elastic member comprises a magneto-viscoelastic elastomer member and an associated variable magnet.

8. The vehicle vibration and noise reducing system according to claim 7, wherein the variable magnet comprises an electromagnet.

9. The vehicle vibration and noise reducing system according to claim 7, wherein the variable magnet comprises a combination of an electromagnet and a permanent magnet.

10. The vehicle vibration and noise reducing system according to claim 7, wherein the sensor comprises a magnetic flux sensor.

11. The vehicle vibration and noise reducing system according to claim 10, wherein the magnetic flux sensor is encapsulated in the elastic member.

12. The vehicle vibration and noise reducing system according to claim 1, wherein the strain sensor is used also for a feedback control of the elastic modulus of the variable elastic member by the elastic member control unit.

* * * * *